United States Patent [19]

Bergmann

[11] Patent Number: 5,275,761

[45] Date of Patent: Jan. 4, 1994

[54] CONDITIONING SHAMPOO COMPOSITION AND METHOD OF PREPARING AND USING THE SAME

[75] Inventor: Wolfgang Bergmann, Highland Park, Ill.

[73] Assignee: Helene Curtis, Inc., Chicago, Ill.

[21] Appl. No.: 869,538

[22] Filed: Apr. 15, 1992

[51] Int. Cl.$^5$ .................. A61K 7/075; C11D 1/12; C11D 1/06

[52] U.S. Cl. .................. 252/551; 252/174.21; 424/70

[58] Field of Search .................. 252/174.21, 551; 424/70

[56] References Cited

U.S. PATENT DOCUMENTS

| | | | |
|---|---|---|---|
| 4,379,755 | 4/1983 | Yamada et al. | 252/312 |
| 4,664,835 | 5/1987 | Grollier et al. | 252/90 |
| 4,704,272 | 11/1987 | Oh et al. | 424/70 |
| 4,741,855 | 5/1988 | Grote et al. | 252/142 |
| 4,788,006 | 11/1988 | Bolich, Jr. et al. | 252/550 |
| 4,902,499 | 2/1990 | Bolich, Jr. et al. | 424/70 |
| 4,948,528 | 8/1990 | Hoeffkes et al. | 252/357 |
| 4,996,059 | 2/1991 | Grollier et al. | 424/71 |
| 5,017,305 | 5/1991 | Hoeffkes et al. | 252/311 |
| 5,077,040 | 12/1991 | Bergmann et al. | 424/70 |
| 5,078,990 | 1/1992 | Martin et al. | 424/70 |
| 5,089,252 | 2/1992 | Grollier et al. | 424/47 |
| 5,145,607 | 9/1992 | Rich | 252/547 |
| 5,180,584 | 1/1993 | Sebag et al. | 424/401 |

FOREIGN PATENT DOCUMENTS

| | | | |
|---|---|---|---|
| 0413417 | 2/1991 | European Pat. Off. | A61K 7/08 |
| WO90/08531 | 8/1990 | PCT Int'l Appl. | A61K 7/08 |
| 2035362 | 6/1980 | United Kingdom | C11D 1/94 |

Primary Examiner—Christine Skane
Assistant Examiner—Michael P. Tierney
Attorney, Agent, or Firm—Marshall, O'Toole, Gerstein, Murray & Borun

[57] ABSTRACT

A conditioning shampoo composition comprising: (a) an anionic cleansing surfactant, such as an alkyl ether sulfate or an alkyl sulfate, like sodium lauryl ether sulfate or ammonium lauryl sulfate; (b) a water-insoluble conditioning agent, such as a silicone compound or a hydrocarbon compound, like a polydimethylsiloxane; (c) an emulsifying composition comprising (i) a polyhydric compound, such as a glycol, a triol or a polyol, and (ii) an anionic emulsifying surfactant having the general structural formula:

$$R_1-O-(A)_x-CH_2-Y^-M^+, \qquad (I)$$

wherein $R_1$ is an alkyl or an aralkyl group wherein the alkyl group includes about 6 to about 22 carbon atoms, A is an alkylene oxide moiety wherein the alkylene group includes one to about four carbon atoms, x is a number in the range of 4 to about 50, Y is sulfate, sulfonate, carbonate or carboxylate, and M is selected from the group consisting of hydrogen, an alkali metal, an alkaline earth metal, ammonium, an alkylammonium or a hydroxyalkylammonium, wherein the alkyl group includes one to about four carbon atoms; and (d) a suspending agent, in (e) a suitable carrier, that effectively resists phase separation and that cleanses the hair and imparts improved wet stage and improved dry stage conditioning properties to the hair in a single application of the composition is disclosed.

38 Claims, No Drawings

CONDITIONING SHAMPOO COMPOSITION AND METHOD OF PREPARING AND USING THE SAME

FIELD OF THE INVENTION

The present invention relates to a conditioning shampoo composition, to its method of preparation and to a method of shampooing hair that cleanses the hair and imparts improved wet stage and improved dry stage conditioning properties to hair in a single application of the composition. More particularly, the present invention is directed to a conditioning shampoo composition including: a) an anionic cleansing surfactant, like an alkyl ether sulfate, such as sodium lauryl ether sulfate; b) a water-insoluble conditioning agent, such as a silicone compound or a hydrocarbon compound, like a polydimethylsiloxane; c) an emulsifying composition comprising (i) a polyhydric compound, such as a glycol, a triol or a polyol, and (ii) an anionic emulsifying surfactant depicted by the general structural formula (I):

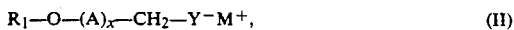

wherein $R_1$ is an alkyl or an aralkyl group including about 6 to about 22 carbon atoms, A is an alkylene oxide moiety wherein the alkylene group includes one to about four carbon atoms, x is a number in the range of 4 to about 50, Y is sulfate, sulfonate, carbonate or carboxylate, and M is selected from the group consisting of hydrogen, an alkali metal, an alkaline earth metal, ammonium, an alkylammonium or a hydroxyalkylammonium, wherein the alkyl group includes one to about four carbon atoms; and d) a suspending agent, in e) a suitable carrier. The composition is prepared by first forming a gel including the emulsifying composition and the water-insoluble conditioning agent; then admixing the gel with the anionic cleansing surfactant, the suspending agent and the carrier. The conditioning shampoo composition effectively cleanses the hair and imparts improved wet stage and dry stage conditioning properties to hair in a single application of the composition. Surprisingly, an aqueous conditioning shampoo composition of the present invention, including a water-insoluble component, effectively resists phase separation. Therefore, the anionic components and the water-insoluble component are available to effectively cleanse the hair and to impart wet stage and dry stage conditioning properties to the hair.

BACKGROUND OF THE INVENTION

Most individuals buy and use a hair shampoo for its cleansing properties. In addition to clean hair, the consumer also desires sufficiently-conditioned hair that holds a preset configuration. However, present-day hair shampoos generally are formulated with highly-effective synthetic surfactants, like anionic surfactants, that primary clean, as opposed to conditioning, the hair. Therefore, it is not surprising that hair shampoos usually neither help detangle wet hair nor impart any residual hair conditioning benefits to dry hair, such as the manageability or styleability of hair sets.

Consequently, after shampooing, the hair normally is left in a cosmetically-unsatisfactory state because an anionic surfactant-based hair shampoo composition not only removes all of the dirt and soil from the hair, but also removes essentially all of the sebum that is naturally present on the surface of the hair fibers. Therefore, the properties of anionic surfactants that effectively cleanse the hair also serve to leave the hair in a cosmetically-unsatisfactory condition. In general therefore, shampooing the hair with a hair shampoo composition including anionic surfactants, leaves the hair, after rinsing with water, with an undesirable harsh, dull and dry touch or feel, usually called "creak".

As a result, thoroughly cleansed hair is extremely difficult to comb, in either the wet or dry stage, because the individual hair fibers tend to snarl, kink and interlock with each other. In addition, incompletely dried hair, such as hair dried with a towel, has poor brushing properties. Then, after complete drying, the hair does not set well, and the combing or brushing property of the dried hair remains poor. The dried hair also has undesirable electrostatic properties in a low humidity atmosphere that cause the hair to "fly away", thereby further reducing the brushing property of the hair. The unsatisfactory combing or brushing property of freshly-shampooed hair also causes hair damage, such as split ends or hair breakage. In addition, the natural luster and resiliency of the hair is reduced.

Accordingly, freshly-shampooed hair usually requires a post-shampoo hair treatment with a conditioning composition to improve the unsatisfactory physical and cosmetic condition of the hair. A conditioning composition normally is applied separately from the hair shampoo, and usually is a rinse or a cream-like lotion containing a cationic compound. Therefore, investigators have sought hair shampoo compositions that both cleanse the hair and leave the hair in a cosmetically-satisfactory state, such that the subsequent treatment with a conditioner composition can be avoided.

Consequently, investigations were directed at providing a composition that behaves both as a shampoo and as a hair conditioner. However, the resulting shampoo-conditioner compositions possessed several disadvantages. For example, it is known in the art that anionic surfactants are suitable hair cleansers, and that, in many instances, cationic surfactants and cationic polymers are suitable hair conditioners. However, the major difficulty encountered by investigators is the inherent incompatibility between an anionic surfactant and a cationic surfactant or cationic polymer. Consequently, contact between the anionic surfactant and the cationic surfactant or cationic polymer either produces an intractable precipitate that forms immediately, or causes an interaction between the anionic and cationic components that significantly reduces their respective cleansing and conditioning properties. The reduction in cleansing and conditioning effectiveness also is observed in compositions wherein the anionic and cationic components do not precipitate from the composition but remain in solution or in a suspended state. This incompatibility between an anionic compound and a cationic compound is well recognized by workers skilled in the art. For example, Sagarin in *Cosmetics*, Interscience Publishers, Inc., New York, p. 538, 1956, states that anionic and cationic compound cannot be used in combination because they react to form insoluble salts. Thus, in practice, consumer needs traditionally have been met by applying a nonsubstantive, anionic surfactant-based shampoo to the hair to cleanse the hair, then rinsing the hair, followed by applying a conditioner composition including a substantive cationic compound to the hair to condition the hair.

While numerous shampoos including a substantive cationic hair conditioner have been disclosed, such shampoos have not been totally satisfactory because of the compatibility problems between anionic cleansing surfactants and cationic conditioning compounds. This compatibility problem has caused workers in the field to examine other surfactants such as nonionics, amphoterics and zwitterionics as a total or partial replacement for the anionic cleansing surfactant. However, the nonionic, amphoteric and zwitterionic surfactants are inferior cleansing surfactants compared to the anionic surfactants.

To avoid the anionic-cationic compatibility problems inherent in a conditioning shampoo that includes an anionic cleansing surfactant and a substantive cationic conditioning compound, to increase the degree of conditioning imparted to the hair, and to maintain the cleansing efficiency of the hair shampoo, investigators sought other classes of compounds that were substantive to the hair and that imparted improved conditioning properties to the hair. These compounds usually are water-insoluble compounds and are nonionic in character. Exemplary compounds include the silicone conditioning agents, the hydrocarbon conditioning agents, the fatty esters and the fatty alcohols including about 8 to about 22 carbon atoms. However, although these compounds avoided the anionic-cationic compatibility problems, these compounds presented the problems of formulating a stable composition that resisted phase separation over the normal life of the product, that effectively delivered the conditioning agent to shampooed hair, and that generated a sufficient foam level for consumer acceptance.

Shampoo-conditioner compositions including silicones have been disclosed in several patents, including U.S. Pat. No. 2,826,551 to Green; U.S. Pat. No. 3,964,500 to Drakoff; U.S. Pat. No. 4,364,837 to Pader; British Pat. No. 849,433 to Woolston; U.S. Pat. No. 4,741,855 to Grote, et al.; U.S. Pat. Nos. 4,788,006 and 4,902,499 to Bolich, Jr. et al. and U.S. Pat. No. 4,704,272 to Oh et al.

A particularly difficult problem encountered in silicone-containing conditioning shampoos is maintaining a dispersed, insoluble silicone material suspended in stable form, while retaining the cleansing and conditioning performance of the conditioning shampoo product. A variety of materials have been proposed for inclusion in silicone-containing conditioning shampoos for purposes of thickening and stabilization such as xanthan gum, long chain acyl derivatives, long chain amide oxides, and long chain alkanolamides, as disclosed in U.S. Pat. Nos. 4,788,006; 4,704,272; and 4,741,855.

Therefore, because hair shampoo compositions are predominantly anionic in character, the incorporation of a substantive cationic compound into an anionic shampoo composition is difficult because of the inherent incompatibility between anionic and cationic surfactants. Similarly, the incorporation of a water-insoluble conditioning agent into an anionic shampoo composition is difficult because of the inherent phase instability between the aqueous-based shampoo and the water-insoluble conditioning agent. Nevertheless, a conditioning shampoo composition is desirable because of the convenience such a combination product offers to the consumer. In such a conditioning shampoo composition, the anionic surfactant acts to rid the hair and scalp of dirt, surface film, debris, and the like, while the water-insoluble conditioning compound deposits on the hair to provide conditioning benefits, such as manageability, shine and texture.

Until the composition and method of the present invention, it has proven very difficult to provide a stable hair conditioning shampoo composition because of the inherent chemical incompatibility between cationic and anionic surfactants, and because of the phase instability of an aqueous composition including a water-insoluble conditioning agent. In accordance with an important feature of the present invention, a particular class of anionic emulsifying surfactants and a water-insoluble conditioning agent are incorporated into a conditioning shampoo composition wherein the composition effectively resists phase separation, and wherein the water-insoluble conditioning agent is effectively deposited on the shampooed hair. The conditioning shampoo, including both an anionic cleansing surfactant and a water-insoluble nonionic conditioning agent, therefore, is utilized to clean the hair and, essentially simultaneously, to impart conditioning properties to the hair.

In accordance with an important feature of the present invention, an anionic emulsifying surfactant depicted by general structural formula (I), e.g., a carboxylated surfactant, is present not only to help cleanse the hair, but also to act, in conjunction with the polyhydric compound, as an emulsifying composition to emulsify the water-insoluble conditioning agent. Furthermore, it has been found that a phase stable conditioning shampoo is provided by the method of preparing the conditioning shampoo of the present invention. In particular, by first preparing a gel including the anionic emulsifying surfactant depicted by general structural formula (I), the polyhydric compound and the water-insoluble conditioning agent, followed by admixing the gel with an aqueous solution of the anionic cleansing surfactant and the suspending agent, a stable emulsion that resists phase separation and that effectively cleanses and conditions the hair, essentially simultaneously, is provided.

Other investigators have disclosed using a preblended gel to incorporate a water-insoluble compound into an aqueous emulsion. For example, Yamada et al., in U.S. Pat. No. 4,379,755, disclose a gel composition including a hydrophilic sucrose fatty acid ester, a polyhydric alcohol and an oil, that provides a phase stable emulsion after dilution with water. Yamada et al. teach the emulsification of a water-insoluble compound utilizing a blend of a nonionic sucrose fatty acid ester and a polyhydric alcohol. Yamada et al. do not teach or suggest solubilizing a water-insoluble compound in a blend of an anionic emulsifying surfactant depicted by general structural formula (I) and a polyhydric alcohol, then diluting the preblended gel with an aqueous solution of a suspending agent and anionic cleansing surfactant to provide an emulsified composition that effectively resists phase separation and that essentially simultaneously cleanses and conditions the hair.

The need for an effective and stable conditioning shampoo composition that cleanses the hair and conditions the hair, i.e., renders the hair more manageable, in a single hair treatment has long been recognized in the art. Accordingly, although conditioning compositions for application to previously-shampooed hair are well known, only recently have conditioning shampoo compositions become available. For example, some conditioning shampoo compositions are specially formulated for mildness, and accordingly low detergency, in order to leave a portion of the natural oils on the hair shaft.

However, hair treated with this type of composition becomes greasy, dirty looking and dirty feeling relatively quickly.

Another difficulty encountered in preparing this type of conditioning shampoo composition has been achieving a stable composition without destroying the delicate balance of conditioning, cleansing, consumer appeal, esthetic properties and other functional properties. Surprisingly and unexpectedly, although a composition of the present invention includes both an anionic cleansing surfactant and a nonionic water-insoluble conditioning agent compound, e.g., a silicone or hydrocarbon, the composition is sufficiently phase stable, lathers sufficiently, cleanses the hair and imparts conditioning properties to the hair without a greasy feeling, while maintaining excellent physical and esthetic properties for consumer appeal.

Therefore, the present invention relates to a conditioning shampoo composition for cleansing the hair and for imparting improved physical and cosmetic properties to the hair, such as improved combing properties, luster and manageability. It is known that anionic surfactants are suitable for shampooing the hair, and that certain water-insoluble nonionic compounds are useful for conditioning the hair. In addition, combining an anionic cleansing surfactant and a nonionic water-insoluble conditioning agent in a conditioning composition has proven difficult because of the phase instability resulting from the water-insoluble conditioning compound. In accordance with an important feature of the present invention, anionic surfactants can be combined with a water-insoluble nonionic conditioning agent, like a silicone or a hydrocarbon conditioning compound, to provide a stable and effective conditioning shampoo composition. As manufactured, the composition is metastable, wherein the term "metastable composition" is defined as a composition that is sufficiently stable to resist phase separation during storage; but, upon application to the hair, deposits a sufficient amount of water-insoluble conditioning components onto the hair shaft to withstand rinsing from the hair during the shampooing and rinsing process, and thereby impart conditioning properties to the hair.

Accordingly, the present invention is directed to a conditioning shampoo composition, including a nonsubstantive and high-foaming anionic cleansing surfactant and a combination of an anionic emulsifying surfactant and a nonionic water-insoluble hair conditioning component, that simultaneously cleanses the hair and imparts desirable physical and cosmetic properties to the hair. After shampooing the hair with the conditioning shampoo composition of the present invention, the hair is combed easily when wet and the hair possesses satisfactory cosmetic properties when dry, including, in particular, elasticity, body, sheen and manageability. In contrast to prior compositions, wherein cationic conditioning compounds were blended primarily with amphoteric surfactants, the conditioning shampoo composition of the present invention includes a nonionic, water-insoluble conditioning agent; an anionic emulsifying surfactant; and an anionic cleansing surfactant to cleanse the hair. Surprisingly, the particular class of anionic emulsifying surfactant utilized in the present invention, in conjunction with the polyhydric compound, effectively emulsifies the water-insoluble conditioning agent, thereby precluding phase separation, and in addition, assists the anionic cleansing surfactant cleanse the hair. Therefore, the stability and incompatibility problems normally encountered when a water-insoluble conditioning agent and anionic surfactant are present in the same aqueous composition have been overcome.

The need for stable shampoo compositions that also condition the hair, e.g., renders the hair more manageable, has long been recognized in the art. The present invention is directed to such a stable conditioning shampoo composition, wherein the aqueous composition includes an anionic cleansing surfactant; a water-insoluble hair conditioning agent, like a silicone compound or a hydrocarbon compound; an emulsifying composition comprising a polyhydric compound and an anionic emulsifying surfactant depicted by the general structural formula (I):

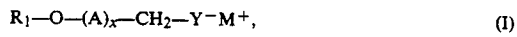

$$R_1-O-(A)_x-CH_2-Y^-M^+, \quad (I)$$

wherein $R_1$ is an alkyl or an aralkyl group including about 6 to about 22 carbon atoms, A is an alkylene oxide moiety wherein the alkylene group includes one to about four carbon atoms, x is a number in the range of 4 to about 50, Y is sulfate, sulfonate, carbonate or carboxylate, and M is selected from the group consisting of hydrogen, an alkali metal, an alkaline earth metal, ammonium, an alkylammonium or a hydroxyalkylammonium, wherein the alkyl group includes one to about four carbon atoms; and a suspending agent, wherein the conditioning shampoo composition effectively resists phase separation and effectively delivers the water-insoluble conditioning agent to the hair.

A composition of the present invention is sufficiently stable to resist phase separation, yet is able to impart conditioning properties to shampooed hair, even though a water-insoluble conditioning agent is present in the aqueous composition. The composition demonstrates an excellent ability to deposit the water-insoluble conditioning agent on the hair because the emulsified water-insoluble conditioning agent is present in the composition in a particle size that is sufficiently large to deposit on the hair, yet is sufficiently small to resist phase separation. Therefore, and in accordance with the present invention, the hair is cleansed and, essentially simultaneously, hair conditioning properties are imparted to the hair by a method of contacting the hair with an aqueous composition comprising an anionic cleansing surfactant, a water-insoluble conditioning agent, an emulsifying composition including a polyhydric compound and an anionic emulsifying surfactant depicted by general structural formula (I), and a suspending agent. The stable composition results from both the particular ingredients included in the composition and the method of preparing the composition. The composition of the present invention both cleanses the hair and conditions the hair to provide more manageable and esthetically-pleasing hair in a single application of the shampoo-conditioner composition to the hair.

SUMMARY OF THE INVENTION

In brief, the present invention relates to a conditioning shampoo composition, a method of preparing the composition and a method of shampooing and conditioning hair. More particularly, the present invention relates to a method of shampooing the hair, whereby the hair is cleansed and conditioned, essentially simultaneously, by contacting the hair with a composition comprising an anionic cleansing surfactant, a water-insoluble conditioning compound, an emulsifying composition including a polyhydric compound and an anionic emulsifying surfactant depicted by general structural formula (I), and a suspending agent in a suitable carrier. Optionally, an amphoteric surfactant, like a betaine or a hydroxysultaine, or a nonionic surfactant, like an alkanolamide, can be included in the composition to improve the esthetic properties and consumer appeal of the composition.

Treating the hair with single application of an aqueous composition including an anionic cleansing surfactant, such as an alkyl ether sulfate, like sodium lauryl ether sulfate; a water-insoluble conditioning agent, such as a silicone compound or a hydrocarbon compound, like a polydimethylsiloxane; an emulsifying composition including a polyhydric compound, such as a glycol, a triol or a polyol, like glycerin; and an emulsifying surfactant depicted by general structural formula (I), such as an anionic fatty carboxylated surfactant, like sodium trideceth-7 carboxylate; and a suspending agent, effectively cleanses the hair and simultaneously imparts excellent wet stage and excellent dry stage conditioning properties to the hair. Surprisingly and unexpectedly, hair shampooed with an easy-to-apply anionic surfactant-based composition of the present invention is thoroughly cleansed and exhibits improved physical and cosmetic softness and body.

Therefore, one aspect of the present invention is to provide a conditioning shampoo composition that cleanses the hair and imparts improved physical properties and cosmetic properties to the hair in a single application of the composition to the hair.

Another aspect of the present invention is to provide a conditioning shampoo composition, comprising an anionic cleansing surfactant; a water-insoluble conditioning agent; an emulsifying composition including a polyhydric compound and an anionic emulsifying surfactant depicted by general structural formula (I); and a suspending agent, in a suitable carrier comprising water, and optionally, an amphoteric surfactant, a nonionic surfactant or a combination thereof.

Another aspect of the present invention is to provide a conditioning shampoo composition that effectively resists phase separation, demonstrates extended product stability, exhibits excellent cleansing properties and effectively delivers the conditioning compounds to the hair or scalp to impart conditioning properties thereto.

Another aspect of the present invention is to provide a method of treating hair with a conditioning shampoo composition to cleanse the hair and to improve the condition of the hair with a single application of the composition to the hair.

Another aspect of the present invention is to provide a method of shampooing hair comprising contacting the hair with a composition including an anionic cleansing surfactant, a water-insoluble conditioning agent, an emulsifying composition including a polyhydric compound and an anionic emulsifying surfactant depicted by general structural formula (I), and a suspending agent, in a suitable carrier comprising water, and optionally, an amphoteric surfactant, a nonionic surfactant or a combination thereof; rinsing the hair; then drying the hair, to cleanse the hair and, essentially simultaneously, to impart improved physical and cosmetic conditioning properties to the hair in a single application of the composition.

Yet another aspect of the present invention is to provide a method of shampooing hair to yield cleansed hair and unexpectedly well-conditioned hair by contacting the hair with an aqueous composition comprising about 5% to about 30% by weight of an anionic cleansing surfactant; an emulsifying composition including about 0.2% to about 15% by weight of the total composition of a polyhydric compound and about 0.05% to about 0.5% by weight of the total composition of an anionic emulsifying surfactant depicted by general structural formula (I); about 0.1% to about 8% by weight of a water-insoluble conditioning agent; and about 0.1% to about 1% by weight of a suspending agent; rinsing the hair; and then drying the hair.

Another aspect of the present invention is to provide a method of shampooing hair to yield cleansed hair and unexpectedly well-conditioned hair by contacting the hair with an aqueous composition comprising: (a) from about 5% to about 30% by weight of an anionic cleansing surfactant; (b) from about 0.1% to about 8% by weight of a water-insoluble conditioning agent, such as a silicone conditioning agent, a hydrocarbon conditioning agent, a fatty alcohol, a fatty ester, or a combination thereof, wherein the fatty alcohol or fatty ester includes a fatty alkyl group having about 8 to about 22 carbon atoms; (c) an emulsifying composition including about 0.1% to about 15% by weight of the total composition of a polyhydric compound and about 0.05% to about 0.5% by weight of the total composition of an anionic emulsifying surfactant depicted by general structural formula (I), such as an anionic carboxylated surfactant, like sodium trideceth-7 carboxylate; and (d) a suspending agent, and, optionally, 0% to about 5% by weight of an amphoteric surfactant, such as a betaine or a hydroxypropylsultaine, or 0% to about 5% by weight of a nonionic surfactant, like an alkanolamide, or a combination thereof; rinsing the hair; and then drying the hair.

Another aspect of the present invention is to provide a method of shampooing hair to yield, in a single hair treatment, cleansed and unexpectedly well-conditioned hair by contacting the hair with an aqueous composition comprising about 5% to about 30% by weight of an anionic cleansing surfactant; about 0.1% to about 8% by weight of a polydimethylsiloxane as the water-insoluble conditioning agent; an emulsifying composition including about 0.2% to about 15% by weight of the total composition of glycerin as the polyhydric compound and about 0.05% to about 0.5% by weight of the total composition of sodium trideceth-7 carboxylate or sodium $C_{12-15}$ pareth-7 carboxylate, or a combination thereof, as the anionic emulsifying surfactant; and about 0.1% to about 1% of methocel, di(hydrogenated tallow) phthalic acid amide, a crosslinked maleic anhydride-methyl vinyl ether copolymer, a primary amine including a fatty alkyl moiety of at least 16 carbon atoms, a secondary amine including two fatty alkyl moieties each having at least 12 carbon atoms, such as, for example, dipalmitoylamine and di(hydrogenated tallow)amine, or a combination thereof, as the suspending agent; rinsing the hair; and then drying the hair.

Another aspect of the present invention is to provide a method of manufacturing a phase stable, aqueous conditioning shampoo composition comprising an anionic cleansing surfactant; a water-insoluble conditioning agent, like a silicone conditioner or a hydrocarbon conditioner; an emulsifying composition including a polyhydric compound and an anionic emulsifying surfactant depicted by general structural formula (I); and a suspending agent including the steps of:

(a) preparing a homogeneous blend of the polyhydric compound and the anionic emulsifying surfactant depicted by general structural formula (I);

(b) admixing the homogeneous blend of step (a) with a water-insoluble conditioning agent to form a gel having a viscosity of at least 5000 cps; and (c) admixing the gel of step (b) with an anionic cleansing surfactant, a suspending agent and water with to provide an emulsified conditioning shampoo composition of the present invention.

Still another aspect of the present invention is to provide a new and improved conditioning shampoo composition capable of effectively cleansing the hair and imparting improved physical, cosmetic and esthetic conditioning properties both to normal hair and to tinted, frosted, bleached or other substantially-damaged hair.

The above and other aspects and novel features of the present invention will become apparent from the following detailed description of the preferred embodiments.

DETAILED DESCRIPTION OF THE INVENTION

A conditioning shampoo composition of the present invention comprises an anionic cleansing surfactant; a water-insoluble hair conditioning compound; an emulsifying composition including a polyhydric compound and an anionic emulsifying surfactant depicted by general structural formula (I); and a suspending agent, in a suitable carrier comprising water. In accordance with an important feature of the present invention, the conditioning shampoo composition includes an anionic cleansing surfactant, an anionic emulsifying surfactant and a substantive nonionic water-insoluble conditioning agent to both cleanse and condition the hair in a single application of the composition to the hair.

Surprisingly and unexpectedly, the conditioning shampoo composition demonstrates sufficient stability in regard to resisting phase separation of the water-insoluble conditioning agent from the aqueous composition and sufficient instability to deposit the water-insoluble conditioning compound on the shampooed hair and resist rinsing from the hair. Optionally, an amphoteric surfactant, or a nonionic surfactant, or a combination thereof, can be included in the composition to impart improved physical properties, and therefore enhanced consumer appeal, to the composition.

The easy-to-apply composition effectively cleanses the hair and, because of the nonionic agent present in the composition, imparts excellent wet comb and dry comb conditioning properties to the hair. In general, the cleansed hair demonstrates improved physical and cosmetic conditioning properties, such as gloss, thickness, softness, manageability and body. As will be demonstrated more fully hereinafter, it is surprising and unexpected for a composition of the present invention, including an anionic cleansing surfactant, an anionic emulsifying surfactant and a water-insoluble conditioning compound, to exhibit such excellent composition stability in regard to phase separation, and to cleanse the hair and impart such improved conditioning properties to the hair in a single application of the composition to the hair.

The anionic cleansing surfactant used in the composition and method o the present invention includes any of the anionic surfactants known or previously used in the art of hair shampoos. An anionic cleansing surfactant is a necessary ingredient in the composition of the present invention because it effectively cleanses the hair and generates a high, stable, foam level that consumers equate with cleaning efficiency. Nonionic and amphoteric surfactants generally are not as effective in cleansing the hair and do not provide the high foam level desired by consumers. Therefore, nonionic and amphoteric surfactants are unsatisfactory as the primary cleansing surfactant in a composition of the present invention. However, optionally, nonionic or amphoteric surfactants can be included in a composition of the present invention to help increase and stabilize foam, to provide a suitable composition viscosity, or to furnish functional or esthetic properties to the composition.

Usually, the anionic cleansing surfactant includes a hydrophobic moiety, such as a carbon chain including about eight carbon atoms to about 30 carbon atoms, and particularly about twelve carbon atoms to about twenty carbon atoms; and further includes a hydrophilic moiety, such as sulfate, sulfonate, carbonate, phosphate or carboxylate. Often, the hydrophobic carbon chain is etherified, such as with ethylene oxide or propylene oxide, to impart a particular physical or reduced surface tension, to the anionic cleansing surfactant.

The anionic cleansing surfactants are well-known and have been widely used in the art of hair shampoos. Therefore, suitable anionic cleansing surfactants include but are not limited to, compounds in the classes known as alkyl sulfates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatty taurides, sulfated monoglycerides, fatty acid amido polyoxyethylene sulfates and isothienates; or combinations thereof. Many additional anionic cleansing surfactants are described in McCUTCHEON'S, DETERGENTS AND EMULSIFIERS, 1989 ANNUAL, published by McCutcheon Division, MC Publishing Co., and incorporated herein by reference.

Usually, the anionic cleansing surfactant is present in the composition as a neutralized salt in the form of a sodium, potassium, lithium, ammonium, alkylammonium or hydroxyalkylammonium salt, wherein the alkyl moiety includes one to about three carbon atoms. The alkyl sulfates and alkyl ether sulfates are particularly effective classes of anionic cleansing surfactants. Consequently, exemplary anionic cleansing surfactants useful in the composition and method of the present invention include, but are not limited to, the ammonium, monoethanolamine, diethanolamine, triethanolamine, isopropylamine, sodium, potassium, lithium or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. An example of an especially useful anionic cleansing surfactant is a combination of a lauryl sulfate salt and a lauryl ether sulfate salt.

In accordance with an important feature of the present invention, the anionic cleansing surfactant is present in the composition in an amount of about 5% to about 30% by weight of the composition. If the anionic cleansing surfactant is present in an amount of less than about 5% by weight of the composition, then the hair is not sufficiently cleansed upon contact with a composition of the present invention. Furthermore, if the anionic cleansing surfactant is present in an amount greater than about 30% by weight of the composition, the conditioning shampoo composition is not adversely affected, but the excess amount of anionic cleansing surfactant does not enhance cleansing of the hair, is simply rinsed from the hair and thereby is wasted. An excess amount of anionic cleansing surfactant, i.e., greater than 30% by weight, may sufficiently solubilize a portion of the water-insoluble conditioning compound, therefore making the solubilized portion essentially unavailable for deposition onto the hair shaft during shampooing.

The anionic cleansing surfactant is included in the conditioning shampoo composition of the present invention in a preferred amount of about 7% to about 20% by weight of the composition, and to achieve the full advantage of the present invention, about 9% to about 18% by weight of the composition. Furthermore, surprisingly and unexpectedly, even when such a low amount of anionic cleansing surfactant is included in the composition, the presence of the water-insoluble conditioning agent does not adversely affect the generation of an acceptable and stable foam level for consumer acceptance.

In accordance with another important feature of the present invention, the conditioning shampoo composition includes an emulsifying composition that effectively emulsifies a water-insoluble conditioning agent in the anionic surfactant-based shampoo. The emulsifying composition includes a polyhydric compound and an anionic emulsifying surfactant depicted by general structural formula (I). The polyhydric compound and the anionic emulsifying surfactant provide a phase stable composition.

The polyhydric compound serves to couple the anionic emulsifying surfactant depicted by general structural formula (I) and the water-insoluble conditioning agent and thereby provide a gel that subsequently is diluted with an aqueous solution of the anionic cleansing surfactant, the suspending agent and the remaining water-soluble composition components. Polyhydric compounds useful in the composition and method of the present invention include, for example, glycols, triols and polyols. The particular identity of the polyhydric compound is not limited as long as the polyhydric compound provides a gel having a viscosity of at least 5000 cps, and preferably of about 10,000 cps to about 60,000 cps. The viscosity of the gel is directly related to the diameter of the droplets of the emulsified water-insoluble conditioning agent present in the conditioning shampoo composition. A gel viscosity of about 10,000 cps to about 18,000 cps provides an emulsified composition wherein the dispersed droplets of the water-insoluble conditioning agent have a diameter of about $5\mu$ (microns) to about $50\mu$, and preferably about $10\mu$ to about $40\mu$. Emulsified droplets of the water-insoluble conditioning agent having a diameter of about $5\mu$ to about $50\mu$ are sufficiently large for efficient deposition onto the shampooed hair, e.g., they are not readily rinsed from the hair during the shampooing, and are sufficiently small to remain suspended in the conditioning shampoo composition, e.g., they effectively resist phase separation during storage.

Specific examples of useful polyhydric compounds include, but are not limited to, ethylene glycol, propylene glycol, butylene glycol, isobutylene glycol, hexylene glycol, diethylene glycol, triethylene glycol, dipropylene glycol, tripropylene glycol, glycerol, diglycerol, fructose, glucose, neopentyl glycol, pentaerythritol, pinacol, cyclopentanediol, cyclohexanediol, 1,2,6-hexanetriol, hydroxystearyl methylglucamine, inositol, maltitol, mannitol, methyl gluceth-10, methyl gluceth-20, sorbitol, sorbeth-20, sucrose, xylitol, or a polyethylene glycol, a polypropylene glycol or a polyethylene-polypropylene glycol having an average molecular weight up to about 500, or combinations thereof.

In particular, triols and polyols, like, for example, glycerin, 1,2,6-hexanetriol, pentaerythritol, inositol, mannitol and sorbitol, are especially useful in the composition and method of the present invention. These triols and polyols provide an anhydrous gel having a viscosity of at least 5000 cps. In addition, the triols and the diols can be used in combination, or in combination with a polyol. To achieve the full advantage of the present invention, the polyhydric compound is glycerol, or glycerin.

A polyhydric compound is essential to the present invention. Compositions absent a polyhydric compound, like glycerin, do not effectively resist phase separation. In contrast, a composition of the present invention including a polyhydric compound is phase stable because the polyhydric compound, as the continuous phase of the anhydrous gel, provides a hydrophilic medium to disperse the water-insoluble conditioning agent, and therefore the composition resists phase separation under normal storage conditions.

The polyhydric compound, present in an amount of about 0.2% to about 10%, and preferably about 0.5% to about 8%, by weight of the total composition, and about 30% to about 60% by weight of the gel, provides a composition wherein the dispersed droplets of the water-insoluble conditioning agent have a diameter of about $5\mu$ to about $50\mu$, and also imparts some conditioning properties to the shampooed hair. However, the polyhydric compound primarily provides a hydrophilic medium to disperse the water-insoluble conditioning agent. In the gel comprising the emulsifying composition and the water-insoluble conditioning agent, the polyhydric compound preferably is present in an amount of about 35% to about 55%, and to achieve the full advantage of the present invention in an amount of about 40% to about 50%, by weight of the gel.

In addition to the anionic cleansing surfactant and the polyhydric compound, the conditioning shampoo composition also includes an anionic emulsifying surfactant depicted by general structural formula (I) in an amount of about 0.05% to about 0.5%, and preferably from about 0.1% to about 0.4%, by weight of the total composition to emulsify the water-insoluble conditioning agent in the composition and to assist cleansing the hair. In the gel, the anionic emulsifying surfactant is present in an amount of about 1% to about 10%, and preferably from about 2% to about 8%, by weight of the gel. The particular anionic emulsifying surfactants depicted by general structural formula (I) included in a composition manufactured by the present method provide a stable emulsified composition that resists phase separation. Therefore, the anionic cleansing surfactant is available to cleanse the hair and the water-insoluble conditioning compound is available to condition the hair.

In particular, introducing an anionic emulsifying surfactant depicted by general structural formula (I) into the composition provides an emulsifying composition, further including the polyhydric compound, that effectively emulsifies the water-insoluble conditioning compound. Therefore, improved and more durable conditioning properties, such as body and manageability, are imparted to the shampooed hair. Surprisingly and unexpectedly, the present method and composition overcome a major problem encountered in formulating a conditioning shampoo composition, i.e., phase instability due to the presence of a water-insoluble conditioning compound.

Anionic emulsifying surfactants found useful in a composition of the present invention are depicted by the general structural formula (I):

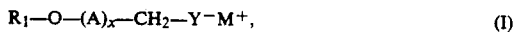

$$R_1-O-(A)_x-CH_2-Y^-M^+, \qquad (I)$$

wherein $R_1$ is an alkyl or aralkyl moiety including about six to about twenty-two carbon atoms; A is an alkylene oxide moiety, wherein the alkylene group includes one to about four carbon atoms; x is a number in the range of four to about fifty; Y is sulfate, sulfonate, carbonate or carboxylate; and M is hydrogen, ammonium, alkylammonium, hydroxyalkylammonium, an alkali metal or an alkaline earth metal, wherein the alkyl moiety includes one to about four carbon atoms. An anionic emulsifying surfactant depicted by general structural formula (I) demonstrates a sufficient ability to emulsify the nonionic water-insoluble conditioning agent, and sufficient ability to cleanse the hair.

A particularly useful class of anionic emulsifying surfactants depicted by general structural formula (I) is exemplified by the anionic carboxylated emulsifying surfactants depicted in structural formula (II):

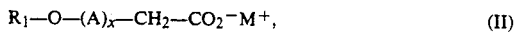

$$R_1-O-(A)_x-CH_2-CO_2^-M^+, \qquad (II)$$

wherein $R_1$, A, x and M are defined as above. Preferably, the anionic emulsifying surfactant is a carboxylated surfactant of structural formula (II), wherein $R_1$ is nonylphenol, octylphenol or an alkyl group including about ten to about sixteen carbon atoms, x is a number in the range of about 5 to about 15, add M is selected from the group consisting of sodium, potassium, hydrogen, ammonium, alkylammonium, hydroxyalkylammonium, and combinations thereof, wherein the alkyl moiety includes one to about three carbon atoms. To achieve the full advantage of the present invention, in the carboxylated emulsifying surfactant of structural formula (II), $R_1$ is an alkyl group including about twelve to fifteen carbon atoms, x is a number in the range of about 6 to about 10, and M is sodium. This particular compound is available commercially under the brand name SURFINE WNT, from Finetex Inc., Elmwood Park, N.J., and has a designation given by The Cosmetic, Toiletry and Fragrance Association, Inc. in the *CTFA Cosmetic Ingredient Dictionary*, 3rd.ed., 1982 or in the 1985 Supplement (hereinafter referred to as the *CTFA Dictionary*) as sodium pareth-25-7 carboxylate.

Other useful carboxylated anionic emulsifying surfactants of structural formula (II) include, but are not limited to, compounds having the CTFA designation nonoxynol-10 carboxylic acid, trideceth-7 carboxylic acid, laureth-13 carboxylic acid, $C_{14-15}$ pareth-8 carboxylic acid, $C_{11-15}$ pareth-7 carboxylic acid, $C_{12-13}$ pareth-5 carboxylic acid, $C_{12-15}$ pareth-7 carboxylic acid, ceteareth-25 carboxylic acid, coceth-7 carboxylic acid, deceth-7 carboxylic acid, isosteareth-6 carboxylic acid, isosteareth-11 carboxylic acid, laureth-5 carboxylic acid, laureth-10 carboxylic acid, trideceth-4 carboxylic acid, trideceth-15 carboxylic acid, trideceth-19 carboxylic acid, and combination thereof, including the alkali metal, alkaline earth metal, ammonium, alkylammonium and hydroxyalkylammonium salts thereof. Such compounds are available commercially under the brand name SURFINE from Finetex, Inc., Elmwood Park, N.J. and under the brandname SANDOPAN from Sandoz Inc., East Hanover, N.J.

The anionic emulsifying surfactants depicted by general structural formula (I) have demonstrated an excellent compatibility with the other hair shampoo-conditioning composition ingredients of the present invention, and an ability to help generate and maintain an excellent foam level, or foam height, even in the presence of other ingredients in the hair shampoo-conditioner composition of the present invention, i.e., the water-insoluble conditioning agent, that have a tendency to reduce or eliminate the foaming properties of the composition. It should be noted that although the generation of a copious and stable foam is not directly related to the cleaning ability of a composition, the generation of a copious and stable foam by a hair shampoo composition is especially important to achieve consumer acceptance of the product because the consumer equates cleaning efficiency with the generation of a high, stable foam.

In general, however, any anionic emulsifying surfactant depicted by general structural formula (I) can be included in the composition of the present invention as long as the resistance to phase separation; the ability to solubilize and emulsify the nonionic water-insoluble conditioning agent; the cleansing efficiency; the conditioning efficiency; and the foam generation capabilities of the composition are not adversely affected. Therefore, examples of other anionic emulsifying surfactants useful in a composition of the present invention include, but are not limited to, a $C_{12-15}$ pareth sulfate, a laureth-5 sulfate, a laureth-7 sulfate, a laureth-12 sulfate, a nonoxynol-4 sulfate, and similar anionic emulsifying surfactants depicted by general structural formula (I) and listed in the *CTFA Cosmetic Ingredient Handbook*, 1st Edition, (1988), pp. 87-94, herein incorporated by reference.

The anionic emulsifying surfactant depicted by general structural formula (I) is present in the conditioning shampoo composition in an amount of about 0.05% to about 0.5% by weight of the total composition. Preferably, the anionic emulsifying surfactant is present in an amount of about 0.1% to about 0.4% by weight of the total composition. The anionic emulsifying surfactant is present in the gel comprising the polyhydric compound, the anionic emulsifying surfactant and the water-insoluble conditioning agent in an amount of about 1% to about 10%, and preferably about 2% to about 8%, by weight of the gel. The anionic emulsifying surfactant is present in the conditioning shampoo composition in a sufficient amount, e.g., about 0.05% to about 0.5% by weight of the composition, to help cleanse shampooed hair. However, the primary function of the anionic emulsifying surfactant is to assist the polyhydric compound emulsify the water-insoluble conditioning agent. Therefore, when the anionic emulsifying surfactant is present at about 0.05% to about 0.5% by weight of the composition, and is preblended with the polyhydric compound, preferably in a ratio of about 4 to 1 about 50 to 1, and to achieve the full advantage of the present invention, about 5 to 1 to about 25 to 1, of polyhydric compound to anionic emulsifying surfactant, the preblend is an effective emulsifying composition for the water-insoluble conditioning agent and provides a stable conditioning shampoo composition.

In addition to the anionic cleansing surfactant, the polyhydric compound and the anionic emulsifying surfactant depicted by general structural formula (I), the conditioning shampoo composition also includes a water-insoluble conditioning agent. In particular, the water-insoluble conditioning agent is a nonionic compound, such as for example a silicone conditioning compound, a hydrocarbon conditioning compound, a fatty ester or a fatty alcohol, wherein the fatty alkyl group includes about 8 to about 22 carbon atoms. To achieve the full advantage of the present invention, the water-insoluble conditioning agent is a silicone conditioning compound, either volatile or nonvolatile, or a combination thereof. The water-insoluble conditioning agent is included in the composition in an amount of about 0.1% to about 8% by weight of the composition. Preferably, the water-insoluble conditioning compound is present in an amount of about 1% to about 6% by weight of the composition. The water-insoluble conditioning agent is present in the gel in an amount of about 40% to about 70%, and preferably about 45% to about 65%, by weight of the gel.

In one embodiment of the present invention, the conditioning-shampoo composition includes a nonvolatile silicone conditioning compound as the water-insoluble conditioning agent. The nonvolatile silicone can be, for example, a polyalkyl siloxane, a polyaryl siloxane or a polyalkylaryl siloxane. Mixtures of these silicone conditioning compounds also are useful. The preferred nonvolatile silicone is a nonvolatile polydimethylsiloxane compound, such as a mixture, in about a 2:1 weight ratio, of a low molecular weight polydimethylsiloxane fluid and a higher molecular weight polydimethylsiloxane gum. Preferred silicone gums include linear and branched polydimethylsiloxanes of the following general formula:

$(CH_3)_3SiO-[Si(CH_3)_2O]_n-Si(CH_3)_3$, wherein n is a number from about 2,000 to about 15,000, and preferably from about 2,000 to about 7,000. Silicone gums useful in compositions of the present invention are available from a variety of commercial sources, including General Electric Company, Waterford, N.Y. and Dow Corning Corp., Midland, Mich.

The nonvolatile polydimethylsiloxane agent is added to the composition of the present invention in an amount sufficient to impart improved combing and improved feel, such as softness, to the hair after shampooing. As referred to herein, useful nonvolatile silicones are those nonfunctional siloxanes or siloxane mixtures having a viscosity of about 5 to about 600,000 cs (centistokes), and preferably about 350 to about 10,000 cs, at 25° C. The so-called "rigid silicones", as described in U.S. Pat. No. 4,902,499, herein incorporated by reference, having a viscosity above 600,000 cs at 20° C., e.g., 700,000 cs plus, and a weight average molecular weight of at least about 500,000, also are useful in a composition of the present invention.

In another embodiment, the water-insoluble conditioning agent is a volatile silicone conditioning compound. The volatile silicone normally is a low molecular weight polydimethylsiloxane compound, however a low molecular weight polydimethylsiloxane including phenyl substituents also is useful in the compositions of the present invention. Furthermore, the low molecular weight polydimethylsiloxane compound can be a linear or a cyclic polydimethylsiloxane compound. The volatile polydimethylsiloxane compound provides sufficient lubrication and imparts hair conditioning properties to wet hair, and has sufficient volatility to slowly volatilize from the hair such that a residual buildup of silicone compound is not present on dry hair.

An example of a linear, low molecular weight, volatile polydimethylsiloxane compound useful in the composition and method of the present invention is the compound named in the CTFA Dictionary as hexamethyldisiloxane, available commercially under the tradename DOW CORNING 200 FLUID, from Dow Corning Corp., Midland, Mich. Hexamethyldisiloxane has a viscosity of 0.65 cs (centistokes), is highly volatile, is nongreasy, provides lubrication, and improves the overall combing properties of the hair. Other linear polydimethylsiloxanes, such as decamethyltetrasiloxane, having a boiling point of about 172° C. and a viscosity of 2.5 centistokes; octamethyltrisiloxane; and dodecamethylpentasiloxane, also are useful in the composition of the present invention.

In addition, cyclic, volatile polydiemthylsiloxanes, designated in the CTFA Dictionary as cyclomethicones, also are useful in the composition and method of the present invention. The cyclomethicones are low molecular weight, water-insoluble cyclic compounds having an average of about 3 to about 6—[O—Si(CH$_3$)$_2$]— repeating group units per molecule and boil at atmospheric pressure in a range of from about 150° C. to about 250° C. Suitable cyclomethicones are available commercially under the tradenames SILICONE SF.1173 (octamethylcyclotetrasiloxane) and SILICONE SF-1202 (decamethylcyclopentasiloxane) from General Electric, Waterford, N.Y., and SILICONE 334 FLUID and SILICONE 345 FLUID from Dow Corning Corporation, Midland, Mich., the tetramer being listed first in each instance. The cyclic volatile silicones can be used in the present compositions in combination with a linear volatile silicone, and the volatile silicone conditioner can be used in conjunction with the nonvolatile silicone conditioner.

Another suitable water-insoluble conditioning agent useful in the composition of the present invention is a nonvolatile hydrocarbon conditioner, such as mineral oil. The nonvolatile hydrocarbons provide many of the same benefits as the silicone conditioning compounds, and can be included in the composition in conjunction with a silicone conditioning compound.

In another embodiment, the water-insoluble conditioning agent is a volatile hydrocarbon conditioner, such as a hydrocarbon including about 10 carbon atoms to about 26 carbon atoms, that has sufficient volatility to slowly volatilize from the hair to prevent a residual buildup of hydrocarbon on dry hair. The volatile hydrocarbon provides essentially the same benefits as the volatile silicone, such as lubrication and wet hair conditioning.

The preferred volatile hydrocarbon compound is an aliphatic hydrocarbon including about 12 to about 24 carbon atoms, and has a boiling point in the range of from about 100° C. to about 300° C. Exemplary volatile hydrocarbons are depicted in general structural formula (V), wherein n ranges from 2 to 5.

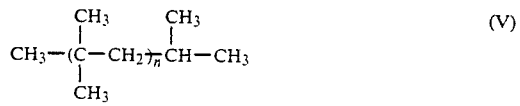

Examples of volatile hydrocarbons useful in the compositions of the present invention are the commercially-available compounds PERMETHYL 99A and PERMETHYL 101A, corresponding to compounds of general structure (V) wherein n is 2 and 3, respectively, from Permethyl Corporation, Frazer, Pa. A volatile hydrocarbon compound is useful in the conditioning shampoo composition of the present invention either alone, or in combination with another volatile or nonvolatile hydrocarbon, or in combination with a volatile or nonvolatile silicone.

In another embodiment, the water-insoluble conditioning agent is a fatty alcohol, wherein the fatty alcohol includes about 8 to about 22, and preferably about 12 to about 22, carbon atoms. Exemplary fatty alcohols include, but are not limited to, lauryl alcohol, oleyl alcohol, myristyl alcohol, tallow alcohol, cetyl alcohol, stearyl alcohol, cetearyl alcohol, behenyl alcohol, and combinations thereof. A fatty alcohol can be used alone, or in combination with a silicone conditioning agent or a hydrocarbon conditioning agent.

In another embodiment, the water-insoluble conditioning agent is a fatty ester. The fatty component of the fatty ester can be derived from a fatty acid or a fatty alcohol, or a combination thereof. In addition, the fatty ester can be a straight fatty ester, like isopropyl myristate; a branched chain fatty ester, like Purcellin Oil; a benzoate ester, like $C_{12-15}$ alcohols benzoate; or a combination thereof.

For example, a useful class of fatty esters is derived from carboxylic acids having about six to about 12 carbon atoms, including both branched and straight chain carboxylic acids. In general, the $C_6$ to $C_{12}$ carboxylic acid is esterified with a fatty alcohol including about 12 to about 22 carbon atoms to provide a fatty ($C_{12}$ to $C_{22}$) ester of a $C_6$ to $C_{12}$ carboxylic acid that is useful in the present invention. Such fatty alcohols include, but are not limited to, lauryl alcohol, myristyl alcohol, cetyl alcohol, cetearyl alcohol, stearyl alcohol, isostearyl alcohol, oleyl alcohol, tallow alcohol, behenyl alcohol and mixtures thereof. Accordingly, fatty ($C_{12}$ to $C_{22}$) esters of $C_6$ to $C_{12}$ carboxylic acids useful in the composition and method of the present invention include, but are not limited to, cetyl octanoate, stearyl heptanoate, stearyl caprylate, stearyl octanoate, lauryl octanoate, myristyl heptanoate and oleyl octanoate, or mixtures thereof. These fatty esters can occur naturally or can be synthesized.

In place of, or in combination with, the fatty ($C_{12}$ to $C_{22}$) ester of a $C_6$ to $C_{12}$ carboxylic acid, a fatty ester derived from a fatty acid including about eight to about 22 carbon atoms esterified with an alcohol including one to about six carbon atoms can be included in the composition of the present invention. Examples of such fatty esters include, but are not limited to, isopropyl myristate, isopropyl palmitate, isopropyl laurate, isopropyl linoleate, isopropyl isostearate, isopropyl oleate, isopropyl stearate, isopropyl tallowate, isopropyl ricinoleate, methyl laurate, methyl linoleate, methyl myristate, methyl stearate, methyl ricinoleate, methyl caprylate, methyl oleate, methyl palmitate, methyl stearate, methyl behenate, methyl soyate, methyl tallowate, isopropyl behenate, isopropyl soyate, propyl oleate, butyl oleate, butyl stearate, methyl coconate, methyl lardate, isobutyl palmitate, butyl myristate, ethyl palmitate, ethyl myristate, ethyl oleate, ethyl stearate, isobutyl stearate, isobutyl myristate and combinations thereof.

Another class of fatty esters that can be included in the composition of the present invention, either alone or in combination with the fatty esters described above, is the benzoate esters. Suitable benzoate esters include esters of benzoic acid wherein the esterifying alcohol includes about eight carbon atoms to about 22 carbon atoms. Examples of suitable benzoate esters include, but are not limited to, the commercial products FINSOLV TN, benzoic acid esterified with fatty alcohols including about 12 to about 15 carbon atoms; FINSOLV SB, isostearyl benzoate, FINSOLV P, PPG-15 stearyl ether benzoate; or combinations thereof, all available from Finetex Inc., Elmwood Park, N.J.

The above-described nonvolatile and volatile silicones, nonvolatile and volatile hydrocarbon compounds, fatty alcohols and fatty esters and have been used in hair-treating compositions and in various other cosmetic compositions, such as antiperspirants, deodorants, hair sprays, hair coloring products, hair grooming products, powder and color products and stick products because their low surface tension provide a light, silky feel on hair and skin. However, it is both new and unexpected for such water-insoluble conditioning agents, as described above, to be combined with an anionic cleansing surfactant, an anionic emulsifying surfactant, a polyhydric compound and a suspending agent to provide an emulsified conditioning shampoo composition that imparts improved wet stage properties, dry stage properties, rinsing properties and overall conditioning benefits to treated hair, like a reduction of split ends, improved body and improved manageability; that effectively cleanses the hair; that generates a sufficient and stable foam volume; and that effectively resists phase separation over the expected life of the composition.

In addition to the anionic cleansing surfactant, the emulsifying composition including the polyhydric compound and the anionic emulsifying surfactant, and the water-insoluble conditioning agent, the conditioning shampoo compositions of the present invention also include about 0.1% to about 1%, and preferably about 0.2% to about 0.8%, by weight of the composition of a suspending agent. The suspending agent can be either a monomeric or a polymeric compound, and either a nonionic or an ionic compound. However, if the suspending agent is an ionic compound the charge density should be sufficiently low such that the suspending agent does not interact with other components of the conditioning shampoo composition.

Accordingly, nonionic suspending agents such as methylcellulose, hydroxybutyl methylcellulose, hydroxypropylcellulose, hydroxypropyl methylcellulose, hydroxyethyl ethylcellulose and hydroxyethylcellulose are useful in a composition of the present invention. Also, a primary amine including a fatty alkyl moiety having at least 16 carbon atoms, like, for example, palmitamine or stearamine, or a secondary amine including two fatty alkyl moieties each having at least 12 carbon atoms, like, for example, dipalmitoylamine or di(hydrogenated tallow)amine, are useful suspending agents. Similarly, the compound di(hydrogenated tallow) phthalic acid amide, available commercially under the brandname KESSCO TAB-2 from Stepan Chemical Co., Northfield, Ill. is a useful suspending agent. A particularly useful suspending agent is STABILEZE ™ 06, a crosslinked maleic anhydride-methyl vinyl ether copolymer, available from ISP Chemicals, Wayne, N.J. STABILEZE ™ 06 provides a composition having excellent esthetic properties, whereas a suspending agent such as methocel provides a useful composition, but the composition including methocel can exhibit a stringy consistency that is disfavored by consumers. Polyacrylic acids, such as the CARBOPOL series available from B.F. Goodrich Chemical Co., Cleveland, Ohio, have been found to be unsuitable suspending agents.

The suspending agent is included in the composition to increase the viscosity of the emulsion, and therefore further improve the phase stability of the composition and improve composition esthetics. For example, when the suspending agent is omitted from the composition, the emulsified composition has an unacceptably thin viscosity and phase separation is observed after 2 days of storage at 120° F. However, by including a suspending agent in the composition, a consumer acceptable viscosity for a shampoo composition, e.g., about 3000 to about 7,500 cps, resulted, and the composition was phase stable for the expected lifetime of the composition, e.g., about one year.

In addition to the above-described essential ingredients, other common cosmetic components and additives can be included in the conditioning shampoo composition of the present invention, as long as the basic properties of the composition are not adversely affected. Such optional cosmetic components and additives include, but are not limited to, nonionic surfactants, amphoteric surfactants, fragrances, dyes, hair colorants, opacifiers, pearlescing agents, thickeners, dandruff control agents, hydrotropes, foam stabilizers, solubilizers, preservatives, water softening agents, acids, alkalies, buffers and the like. These optional components and additives usually are present in weight percentages of 0% to less than about 5% by weight each, and usually about 0.1% to about 20% by weight of the composition in total.

For example, to improve consumer acceptance, enhanced shampoo mildness and enhanced composition esthetics can be achieved by optionally including an amphoteric surfactant in the hair shampoo-conditioner in an amount of 0% to about 5% by weight of the composition. Suitable amphoteric surfactants that can be included in the present invention are exemplified by, but are not limited to, betaines, hydroxypropylsultaines and amine oxides, or combinations thereof. Specific nonlimiting examples of useful amphoteric surfactants include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate, or combinations thereof. In general, however, any amphoteric surfactant can be included in the composition of the present invention as long as the stability, the conditioning and the cleansing efficiency of the composition are not adversely affected.

The conditioning shampoo compositions of the present invention also can include nonionic surfactants to help impart esthetic, physical or cleansing properties to the composition. Likewise, the compositions can include other emulsifiers, conditioning agents, inorganic salts, humectants and similar materials to provide the composition with desirable esthetic or physical properties. Generally, such optional ingredients are present in weight percentages of 0% to about 5% each, and 0% to about 20% in total, relative to the total weight of the composition.

Representative nonionic surfactants that can be included in the hair shampoo-conditioner composition of the present invention include esters of polyols or sugars; fatty acid alkanolamides; polyethylene glycols; the ethoxylated or propoxylated alkylphenols; ethoxylated or propoxylated fatty alcohols; and the condensation products of ethylene oxide and long chain amides. These nonionic surfactants, as well as numerous others not cited herein, are well known in the art and are fully described in the literature, such as McCUTCHEON'S, DETERGENTS AND EMULSIFIERS, 1989 Annual Edition, published by McCutcheon Division, MC Publishing Co.

In particular, a nonionic alkanolamide can be included in the composition to enhance composition thickening and to provide foam stability. The alkanolamide can be included in an amount of 0% to about 5% by weight of the composition. Accordingly, suitable alkanolamides include, but are not limited to, those known in the art of hair care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide EEA, oleylamide DEA, tallowamide DEA, lauramide MIPA, tallowamide MEA, isostearamide DEA, isostearamide MEA, and combinations thereof.

The carrier of the hair shampoo-conditioner composition of the present invention is predominantly water, but nonaqueous solvents also can be included to help solubilize composition ingredients that are not sufficiently soluble in water, to adjust the viscosity of the composition or to act as a humectant. A suitable solvent is ethanol. The optional nonaqueous solvents should not adversely affect the ability of the composition to cleanse and condition the hair or adversely affect consumer appeal of the composition. A nonaqueous solvent can be present in the hair shampoo-conditioner composition of the present invention in an amount of 0% to about 5% by weight of the composition.

To achieve the full advantage of the present invention, the conditioning shampoo composition is a relatively viscous mixture that is stable indefinitely at temperatures normally found in commercial product storage and shipping. A composition of the present invention is an emulsion that is stable and that resists phase separation at a temperature of about 20° C. to about 25° C. essentially indefinitely. The compositions also have demonstrated sufficient stability to phase separation or precipitation of ingredients at temperatures normally found in commercial product storage an shipping to remain unaffected for periods of one year or more.

A sufficiently viscous conditioning shampoo composition results from a judicious selection of the anionic cleansing surfactant, the polyhydric compound, the anionic emulsifying surfactant depicted by general structural formula (I), the water-insoluble conditioning agent and the suspending agent. In addition, a stable and efficacious conditioning shampoo composition is provided when the composition is manufactured according to the method of the present invention. In contrast, a simple blending of the essential and optional ingredients does not provide a stable composition having the water-insoluble conditioning agent homogeneously dispersed throughout the composition as emulsified droplets having a diameter of about $5\mu$ to about $50\mu$. Within this range of diameters, the droplets of water-insoluble conditioning agent are sufficiently large to resist rinsing from the hair prior to deposition and are sufficiently small to resist separating from the aqueous shampoo.

Therefore, in accordance with an important feature of the present invention, a conditioning shampoo composition is prepared by first forming an emulsifying composition comprising the polyhydric compound and the anionic emulsifying surfactant. The emulsifying composition preferably is essentially free of water and is formed by simply admixing a polyhydric compound, like glycerin, and an anionic emulsifying surfactant, like sodium pareth-25-7 carboxylate, depicted by structural formula (II), to provide a homogeneous mixture.

Then, a water-insoluble conditioning agent, like a polydimethylsiloxane, is added to the emulsifying composition. The emulsifying composition and water-insoluble conditioning agent are admixed until the ingredients form a homogeneous gel. The gel is an emulsion wherein the polyhydric compound is the continuous phase and the water-insoluble conditioning agent is the dispersed phase. The anionic emulsifying surfactant serves as the emulsifier.

In accordance with an important feature of the present invention, the identity and the amount of the polyhydric compound, the anionic emulsifying surfactant and the water-insoluble conditioning agent are selected such that the gel has a viscosity of at least 5000 cps, and preferably about 10,000 cps to about 60,000 cps. To achieve the full advantage of the present invention, the gel has a viscosity of about 10,000 cps to about 18,000 cps.

It has been found that a gel, having a viscosity of at least 5000 cps to about 18,000 cps, provides an emulsified conditioning shampoo composition wherein the dispersed water-insoluble conditioning agent is present as droplets having a diameter of about $5\mu$ to about $50\mu$. Preferably, the dispersed droplets have a diameter of about $10\mu$ to about $40\mu$. To achieve the full advantage of the present invention, the dispersed droplets have a diameter of about $15\mu$ to about $30\mu$. Dispersed droplets of conditioning agent having such a diameter distribution provide the best balance of properties in regard to deposition of the conditioning agent on a shampooed hair shaft and in regard to phase stability of the conditioning shampoo composition. Preferably, the gel includes less than about 20% water by weight of the gel, in order to effectively emulsify the water-insoluble conditioning agent and to provide a gel having a viscosity of at least 5000 cps. To achieve the full advantage of the present invention, the gel includes less than 10% water by weight of the gel.

In a separate vessel, the suspending agent is solubilized or dispersed in water, either by simply admixing the suspending agent in the water, e.g., if methocel is the suspending agent; or by admixing the suspending agent and a suitable neutralizing agent in the water, e.g., if crosslinked maleic anhydride-methyl vinyl ether copolymer is the suspending agent, sodium hydroxide also is included in the water. The anionic cleansing surfactant then is added to the aqueous solution or dispersion of the suspending agent. Next, the gel and the aqueous solution or dispersion of the suspending agent and anionic cleansing surfactant are admixed to provide an emulsified composition of the present invention. In accordance with an important feature of the present method, heating is not required to emulsify the water-insoluble conditioning agent in the composition. The composition has a viscosity suitable for use as a hair shampoo; effectively resists phase separation; effectively cleanses and conditions the hair; and generates an acceptable and stable foam level.

In accordance with the method of the present invention, a conditioning shampoo composition was prepared, then applied to hair, to demonstrate the ability of a single application of an aqueous composition, comprising an anionic cleansing surfactant; a water-insoluble conditioning agent; an emulsifying composition including a polyhydric compound and an anionic emulsifying surfactant; and a suspending agent, to simultaneously cleanse the hair and impart hair-conditioning properties to the hair. Tests also were performed to demonstrate the stability of the compositions. Although the mechanism of interaction between the essential ingredients that provides a physically and chemically stable composition and that allows a maximum deposition of the nonionic water-insoluble conditioning agent on the hair is not known precisely, it has been theorized, but not relied upon herein, that the method of manufacturing the composition provides a dispersed phase of water-insoluble conditioning agent having a droplet diameter of from about $5\mu$ to about $50\mu$, and emulsified by the anionic emulsifying surfactant and the polyhydric compound.

Accordingly, it has been theorized that the dispersed droplets of water-insoluble conditioning agent are sufficiently small to resist separating from the aqueous shampoo composition. In addition, the droplet diameter distribution of the emulsified water-insoluble conditioning agent is sufficiently large for efficient deposition on the shampooed hair. The anionic cleansing surfactant and anionic emulsifying surfactant also are available to effectively cleanse the hair. Furthermore, salon tests have demonstrated that a stable and sufficiently high foam level is generated during shampooing, thereby providing enhanced consumer appeal, even at the relatively low amounts of anionic cleansing surfactant present in the composition.

To demonstrate the new and unexpected results provided by the conditioning shampoo of the present invention, the following Example 1 was prepared. The method of manufacturing the hair shampoo-conditioner compositions will be discussed in detail hereinafter. The composition of Example 1 illustrates the storage stability of the conditioning shampoo compositions; and the cleansing efficiency and conditioning properties imparted by a composition of the present invention. The weight percentage listed in each of the following examples represent the actual active amount of each ingredient present in the conditioning shampoo composition.

| | EXAMPLE 1 | |
|---|---|---|
| | Ingredient | % by weight (active basis) |
| 1 | Sodium Trideceth Carboxylate[1] | 0.375 |
| 2 | Glycerin | 3.00 |
| 3 | Dimethicone[2] | 4.125 |
| 4 | Ammonium Lauryl Sulfate[3] | 18.00 |
| 5 | Fatty Alcohol Ether Sulfosuccinate[4] | 4.00 |
| 6 | Crosslinked MVE/VA Copolymer[5] | 0.40 |
| 7 | Citric Acid | 0.35 |
| 8 | Cocamide DEA | 4.00 |
| 9 | Fragrance | 0.40 |
| 10 | Ammonium Xylene Sulfonate[6] | 3.00 |
| 11 | Preservatives | q.s |
| 12 | Dye | q.s |

-continued
EXAMPLE 1

| Ingredient | | % by weight (active basis) |
|---|---|---|
| 13 | Deionized Water | q.s |

[1] Anionic emulsifying surfactant, SANDOPAN DTC, from Sandoz Inc., East Hanover, NJ. (70% active);
[2] Added as a blend of 67% polydimethylsiloxane (350 cs) fluid and 33% silicone gum (100% active);
[3] Added as a 40 aqueous solution;
[4] Anionic surfactant, VARSULF SBFA-40 from Sherex Chemical Co., Dublin, Ohio (40% active);
[5] Suspending agent, STABILEZE TM 06, from ISP Chemicals Corp., Wayne, NJ., (100% active);
[6] Added as a 40% aqueous solution.

The composition of Example 1 was prepared by the above-described method wherein composition ingredients 1 and 2 were blended to provide an emulsifying composition. The ingredient 3 was added to the emulsifying composition to provide an a gel having a viscosity of about 14,000 cps. Composition ingredients 4 through 6 and a portion of the deionized water were added in the listed order to a separate vessel. The crosslinked MVE/VA copolymer was solubilized by the water. Then the gel including composition ingredients 1 through 3 was added to the aqueous solution including composition ingredients 4 through 6. After stirring the mixture until homogeneous, the remaining composition ingredients 7 through 13 were added in the listed order to provide the composition of Example 1.

The composition of Example 1 is an emulsified composition having a viscosity of about 5,600 cps, as determined at room temperature using a Brookfield viscometer with RV4 spindle at 20 rpm; a pH of about 5.5; and includes dispersed droplets of dimethicone having a diameter of about 10μ to about 40μ. The composition of Example 1 demonstrated excellent storage stability; and exhibited no phase separation after storage at about 25° C. for an extended time. In contrast, compositions wherein the ingredients 1 through 3 were added to the composition individually, or wherein ingredients 1 and 2 were blended, then the resulting mixture added to the composition followed by the addition of ingredient 3, were unstable. These compositions underwent phase separation about 2 days after preparation. Accordingly, it was demonstrated that first forming the gel imparts stability to the composition, and therefore is an important step in preparing a composition of the present invention.

In accordance with an important feature of the present invention, it has been found that the viscosity of the gel including the polyol, the hydrophilic quaternary ammonium compound and the water-insoluble conditioning agent varies with the amount of the component present in the gel. In turn, gel viscosity is related to the diameter of the droplets of dispersed water-insoluble conditioning agent present in the gel. Finally, the diameter of the dispersed droplets is directly related to the ability of the droplet to deposit on the hair and the ability of the conditioning shampoo to resist phase separation.

The composition of Example 1 was tested for an ability to deposit a water-insoluble conditioning agent on hair during shampooing by applying the compositions of Example 1 to a normal brown tress of hair, then rinsing the composition from the hair. It was observed that the silicone conditioning agent sufficiently deposited on the hair to impart improved conditioning properties to the shampooed tress.

Therefore, in general, hair shampooed with composition of the present invention exhibits improved esthetic properties, which are especially important for consumer acceptance. The method and composition of the present invention also provide the further benefits of not leaving the hair tacky or sticky; imparting body and shine to shampooed hair; not leaving the hair with an oily or greasy appearance; not forming a crust and therefore providing combability; and providing manageable and styleable hair having body. After shampooing, the hair feels natural and thickened, has body, is soft, shiny, manageable, and combable. A composition of the present invention also conditions the scalp as it conditions the hair.

Obviously, many modifications and variations of the invention as hereinbefore set forth can be made without department from the spirit and scope thereof, and therefore only such limitations should be imposed as are indicated by the appended claims.

What is claimed is:

1. A conditioning shampoo composition comprising:
   (a) about 5% to about 30% by weight of an anionic cleansing surfactant selected from the group consisting of an alkyl sulfate, an alkyl ether sulfate, a sulfate ester of an alkylphenoxy polyoxyethylene ethanol, an alpha-olefin sulfonate, a beta-alkyloxy alkane sulfonate, an alkyl arylsulfonate, an alkyl carbonate, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, an isothienate, and combinations thereof;
   (b) about 0.1% to about 8% by weight of a water-insoluble conditioning agent selected from the group consisting of a silicone comprising compound, a hydrocarbon conditioning compound, a fatty ester, a fatty alcohol, and combinations thereof, wherein the fatty alcohol or fatty ester includes a fatty alkyl group having about 8 to about 22 carbon atoms;
   (c) about 0.25% to about 15.5% by weight of an emulsifying composition comprising:
   (i) a polyhydric compound, and
   (ii) an anionic emulsifying surfactant having the structure:

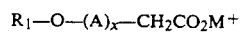

$R_1-O-(A)_x-CH_2CO_2M^+$ wherein $R_1$ is an alkyl or an aralkyl group including about 6 to 22 carbon atoms, A is an alkylene oxide moiety wherein the alkylene group includes one to about four carbon atoms, x is a number in the range of 4 to about 50, and M is selected from the group consisting of hydrogen, an alkali metal, an alkaline earth metal, ammonium, an alkylammonium, a hydroxyalkylammonium, and combinations thereof, wherein the alkyl group includes one to about four carbon atoms; and,
   wherein the polyhydric compound is present in an amount of about 0.2% to about 15% by weight of the total composition, and the anionic emulsifying surfactant is present in an amount of about 0.05% to about 0.5% by weight of the total composition;
   (d) about 0.1% to about 1% by weight of suspending agent; and (e) a suitable carrier comprising water.

2. The composition of claim 1 wherein the anionic cleansing surfactant is present in an amount of about 7% to about 20% by weight of the composition.

3. The composition of claim 1 wherein the water-insoluble conditioning agent is present in an amount of about 1% to about 6% by weight of the composition.

4. The composition of claim 1 wherein the silicone conditioning compound is a nonvolatile silicone conditioning compound having a viscosity of at least 5 centistokes, and is selected from the group consisting of a polyalkyl siloxane, a polyaryl siloxane, a polyalkylaryl siloxane, and combinations thereof.

5. The composition of claim 1 wherein the silicone conditioning compound is a volatile silicone conditioning compound having a boiling point of about 150° C. to about 250°.

6. The composition of claim 1 wherein the hydrocarbon conditioning compound is a volatile hydrocarbon conditioning compound including about 10 to about 26 carbon atoms.

7. The composition of claim 1 wherein the polyhydric compound is a glycol, a triol, a polyol, or a combination thereof.

8. The composition of claim 1 wherein the polyhydric compound is selected from the group consisting of ethylene glycol, propylene glycol, butylene glycol, isobutylene glycol, hexylene glycol, diethylene glycol, triethylene glycol, dipropylene glycol, tripropylene glycol, glycerol, diglycerol, fructose, glucose, neopentyl glycol, pentaerythritol, pinacol, cyclopentanediol, cyclohexanediol, 1,2,6-hexanetriol; hydroxystearyl methylglucamine, inositol, maltitol, mannitol, methyl gluceth-10, methyl gluceth-20, sorbitol, sorbeth-20, sucrose, xylitol, a polyethylene glycol having an average molecular weight up to about 500, a polypropylene glycol having an average molecular weight up to about 500, a polyethylene-polypropylene glycol having an average molecular weight up to about 500, and combinations thereof.

9. The composition of claim 1 wherein $R_1$ is an alkyl or an aralkyl group including about 10 to about 20 carbon atoms, A is an alkylene oxide moiety wherein the alkylene group includes one to about four carbon atoms, and x is a number in the range of 5 to about 15.

10. The composition of claim 1 wherein $R_1$ of the anionic emulsifying surfactant is nonylphenol, octylphenol or an alkyl group including about 10 to about 16 carbon atoms.

11. The composition of claim 9 wherein M is selected from the group consisting of hydrogen, sodium, potassium, ammonium, alkylammonium, hydroxyalkylammonium, and combinations thereof, wherein the alkyl group includes one to about three carbon atoms.

12. The composition of claim 9 wherein $R_1$ is an alkyl group including about 12 to about 15 carbon atoms; x is a number in the range of about 6 to about 10; and M is selected from the group consisting of sodium, potassium, ammonium, alkylammonium, hydroxyalkylammonium, and combinations thereof, wherein the alkyl group includes one to about three carbon atoms.

13. The composition of claim 1 wherein the anionic emulsifying surfactant is selected from the group consisting of pareth-25-7 carboxylic acid, nonoxynol-10 carboxylic acid, trideceth-7 carboxylic acid, laureth-13 carboxylic acid, $C_{14-15}$ pareth-8 carboxylic acid, $C_{11-15}$ pareth-7 carboxylic acid, $C_{12-13}$ pareth-5 carboxylic acid, $C_{12-15}$ pareth-7 carboxylic acid, ceteareth-25 carboxylic acid, coceth-7 carboxylic acid, deceth-7 carboxylic acid, isosteareth-6 carboxylic acid, isosteareth-11 carboxylic acid, laureth-5 carboxylic acid, laureth-10 carboxylic acid, trideceth-4 carboxylic acid, trideceth-15 carboxylic acid, trideceth-19 carboxylic acid, an alkali metal salt thereof, an alkaline earth metal salt thereof, an ammonium salt thereof, an alkylammonium salt thereof, a hydroxyalkylammonium salt thereof, and combinations thereof, wherein the alkylammonium salt or hydroxyalkylammonium salt includes an alkyl group having one to three carbon atoms.

14. The composition of claim 1 wherein the suspending agent is present in an amount of about 0.2% to about 0.8% by weight of the composition.

15. The composition of claim 1 wherein the suspending agent is selected from the group consisting of methylcellulose, hydroxybutyl methylcellulose, hydroxypropylcellulose, hydroxypropyl methylcellulose, hydroxyethyl ethylcellulose, hydroxyethylcellulose, a primary amine including a fatty alkyl moiety having at least 16 carbon atoms, a secondary amine including two fatty alkyl moieties each having at least 12 carbon atoms, di(hydrogenated tallow) phthalic acid amide, a crosslinked maleic anhydride-methyl vinyl ether copolymer, and combinations thereof.

16. The composition of claim 1 further comprising 0% to about 5% by weight of an amphoteric surfactant, 0% to about 5% by weight of a nonionic surfactant, or a combination thereof.

17. The composition of claim 16 wherein the amphoteric surfactant is selected from the group consisting of a betaine, a hydroxypropylsultaine, an amine oxide, and combinations thereof.

18. The composition of claim 16 wherein the nonionic surfactant is selected from the group consisting of an ester of a polyol, an ester of a sugar, a fatty acid alkanolamide, a polyethylene glycol, an ethoxylated fatty alcohol, a propoxylated fatty alcohol, a condensation product of ethylene oxide and a long chain amide, and combinations thereof.

19. The composition of claim 18 wherein the nonionic surfactant is a fatty alkanolamide selected from the group consisting of cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and combinations thereof.

20. The composition of claim 1 wherein the anionic cleansing surfactant is an alkali metal salt, an ammonium salt, an alkylammonium salt or a hydroxyalkylammonium salt, wherein the alkyl group includes from one to about three carbon atoms, of an alkyl sulfate, an alkyl ether sulfate or a combination thereof; the water-insoluble conditioning agent is selected from the group consisting of a nonvolatile silicone having a viscosity of at least 5 centistokes, a volatile silicone having a boiling point of about 150° C. to about 250° C., a volatile hydrocarbon including about 10 to about 26 carbon atoms, and combinations thereof; the polyhydric compound is glycerol; the anionic emulsifying surfactant is sodium pareth-25-7 carboxylate, sodium trideceth carboxylate, or a combination thereof; and the suspending agent is methocel, hydroxypropyl methylcellulose, di(hydrogenated tallow) phthalic acid amide, a crosslinked maleic anhydride-methyl vinyl ether copolymer, a primary amine including a fatty alkyl moiety having at least 16 carbon atoms, a secondary amine including two fatty alkyl moieties each having at least 12 carbon atoms, or a combination thereof.

21. A conditioning shampoo composition comprising:
(a) about 5% to about 30% by weight of an anionic cleansing surfactant selected from the group consisting of alkyl sulfate, an alkyl ether sulfate, a sulfate ester of an alkylphenoxy polyoxyethylene ethanol, an alpha-olefin sulfonate, a beta-alkyloxy alkane sulfonate, an alkyl arylsulfonate, an alkyl carbonate, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, an isothienate, and combinations thereof;
(b) about 0.1% to about 8% by weight of a water-insoluble conditioning agent selected from the group consisting of a nonvolatile silicone having a viscosity of at least 5 centistokes, a volatile silicones having a boiling point of about 150° C. to about 250° C., a volatile hydrocarbon including about 10 to about 26 carbon atoms, and combinations thereof;
(c) about 0.2% to about 15% by weight of a polyhydric compound selected from the group consisting of glycerol, 1,2,6-hexanetriol, pentaerythritol, inositol, mannitol, sorbitol, and combinations thereof;
(d) about 0.05% to about 0.5% by weight of an anionic emulsifying surfactant having the structure:

$$R_1-O-(A)_x-CH_2CO_2^-M^+,$$

wherein $R_1$ is an alkyl or an aralkyl group including about 6 to about 22 carbon atoms, A is an alkylene oxide moiety wherein the alkylene group includes one to about four carbon atoms, x is a number in the range of 5 to about 15, and M is selected from the group consisting of hydrogen, an alkali metal, an alkaline earth metal, ammonium, an alkylammonium, a hydroxyalkylammonium and combinations thereof, wherein the alkyl group includes one to about four carbon atoms;
(e) about 0.1% to about 1% by weight of a suspending agent selected from the group consisting of methocel, hydroxypropyl methylcellulose, di(hydrogenated tallow) phthalic acid amide, a cross-linked maleic anhydridemethyl vinyl ether copolymer, a primary amine including a fatty alkyl moiety having at least 16 carbon atoms, a secondary amine including two fatty alkyl moieties each having at least twelve carbon atoms, and combinations thereof; and
(f) a suitable carrier comprising water.

22. The composition of claim 21 further comprising:
(g) 0% to about 5% by weight of a nonionic alkanolamide selected from the group consisting of cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and combinations thereof.

23. The composition of claim 21 further comprising:
(h) 0% to about 5% by weight of an amphoteric surfactant selected from the group consisting of cocamidopropyl betaine, lauramidopropyl betaine, oleyl betaine, coco/oleamidopropyl betaine, coco betaine, cocamidopropyl hydroxysultaine, tallowamidopropyl hydroxysultaine, dihydroxyethyl tallow glycinate, and combinations thereof.

24. The composition of claim 21 wherein $R_1$ is an alkyl or an aralkyl group including about 10 to about 20 carbon atoms, A is an alkylene oxide moiety wherein the alkylene group includes one to about four carbon atoms, and x is a number in the range of 5 to about 15.

25. A method of treating hair to simultaneously cleans the hair and impart conditioning properties to the hair comprising contacting the hair with a composition comprising:
(a) about 5% to about 30% by weight of an anionic cleansing surfactant selected from the group consisting of an alkyl sulfate, an alkyl ether sulfate, a sulfate ester of an alkylphenoxy polyoxyethylene ethanol, an alpha-olefin sulfonate, a beta-alkyloxy alkane sulfonate, an alkyl arylsulfonate, an alkyl carbonate, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, an isothienate, and combinations thereof:
(b) about 0.1% to about 8% by weight of a water-insoluble conditioning agent selected from the group consisting of a silicone conditioning compound, a hydrocarbon conditioning compound, a fatty ester, a fatty alcohol, and combinations thereof, wherein the fatty alcohol or the fatty ester includes a fatty alkyl group having about 8 to about 22 carbon atoms;
(c) about 0.25% to about 15% by weight of an emulsifying composition comprising:
(i) a polyhydric compound, and
(ii) an anionic emulsifying surfactant having the structure:

$$R_1-O-(A)_x-CH_2CO_2^-M^+,$$

wherein $R_1$ is an alkyl or an aralkyl group including about 6 to about 22 carbon atoms, A is an alkylene oxide moiety wherein the alkylene group includes one to about four carbon atoms, x is a number in the range of 4 to about 50, and M is selected from the group consisting of hydrogen, an alkali metal, an alkaline earth metal, ammonium, an alkylammonium, a hydroxyalkylammonium, and combinations thereof, wherein the alkyl group includes one to about four carbon atoms; and,
wherein the polyhydric compound is present in an amount of about 0.2% to about 15% by weight of the total composition, and the hydrophilic quaternary ammonium compound is present in an amount of about 0.05% to about 0.5% by weight of the total composition;
(d) about 0.1% to about 1% by weight of a suspending agent; and
(e) a suitable carrier comprising water.

26. The method of claim 25 wherein the water-insoluble conditioning agent is present in an amount of about 1% to about 6% by weight of the composition.

27. The method of claim 25 wherein the polyhydric compound is a glycol, a triol, a polyol, or a combination thereof.

28. The method of claim 27 wherein $R_1$ is an alkyl or an aralkyl group including about 10 to about 20 carbon atoms, A is an alkylene oxide moiety wherein the alkylene group includes one to about four carbon atoms, and x is a number in the range of 5 to about 15.

29. The method of claim 25 wherein $R_1$ of the anionic emulsifying surfactant is nonylphenol, octylphenol or an alkyl group including about 10 to about 16 carbon atoms.

30. The method of claim 25 wherein $R_1$ is an alkyl group including about 12 to about 15 carbon atoms; x is a number in the range of about 6 to about 10; and M is selected from the group consisting of sodium, potassium, ammonium, alkylammonium, hydroxyalkylammonium, and combinations thereof, wherein the alkyl group include one to about three carbon atoms.

31. The method of claim 25 wherein the anionic emulsifying surfactant is selected from the group consisting of pareth-25-7 carboxylic acid, nonoxynol-10 carboxylic acid, trideceth-7 carboxylic acid, laureth-13 carboxylic acid, $C_{14\text{-}15}$ pareth-8 carboxylic acid, $C_{11\text{-}15}$ pareth-7 carboxylic acid, $C_{12\text{-}13}$ pareth-5 carboxylic acid, $C_{12\text{-}15}$ pareth-7 carboxylic acid, ceteareth-25 carboxylic acid, coceth-7 carboxylic acid, deceth-7 carboxylic acid, isosteareth-6 carboxylic acid, isosteareth-11 carboxylic acid, laureth-5 carboxylic acid, laureth-10 carboxylic acid, trideceth-4 carboxylic acid, trideceth-15 carboxylic acid, trideceth-19 carboxylic acid, an alkali metal salt thereof, an alkaline earth metal salt thereof, an ammonium salt thereof, an alkylammonium salt thereof, a hydroxyalkylammonium salt thereof, and combinations thereof, wherein the alkyl group includes one to three carbon atoms.

32. The method of claim 25 wherein the suspending agent is selected from the group consisting of methylcellulose, hydroxybutyl methylcellulose, hydroxypropylcellulose, hydroxypropyl methylcellulose, hydroxyethyl ethylcellulose, hydroxyethylcellulose, a primary amine including a fatty alkyl moiety having at least 16 carbon atoms, a secondary amine including two fatty alkyl moieties each having at least 12 carbon atoms, di(hydrogenated tallow) phthalic acid amide, a crosslinked maleic anhydride-methyl vinyl ether copolymer, and combinations thereof.

33. The method of claim 25 further comprising 0% to about 5% by weight of an amphoteric surfactant, 0% to about 5% by weight of a nonionic surfactant, or a combination thereof.

34. The method of claim 33 wherein the amphoteric surfactant is selected from the group consisting of a betaine, a hydroxypropylsultaine, an amine oxide, and combinations thereof.

35. The method of claim 33 wherein the nonionic surfactant is selected from the group consisting of an ester of a polyol, an ester of a sugar, a fatty acid alkanolamide, a polyethylene glycol, an ethoxylated or a propoxylated fatty alcohol, a condensation product of ethylene oxide with a long chain amide and combinations thereof.

36. The method of claim 25 wherein the anionic cleansing surfactant is an alkali metal salt, an ammonium salt, an alkylammonium salt or a hydroxyalkylammonium salt, wherein the alkyl group includes from one to about three carbon atoms, of an alkyl sulfate, an alkyl ether sulfate or a combination thereof; the water-insoluble conditioning agent is selected from the group consisting of a nonvolatile silicone having a viscosity of at least 5 centistokes, a volatile silicone having a boiling point of about 150° C. to about 250° C., a volatile hydrocarbon including about 10 to about 26 carbon atoms, and combinations thereof; the polyhydric compound is glycerol; the anionic emulsifying surfactant is sodium pareth-25-7 carboxylate, sodium trideceth carboxylate, or a combination thereof; and the suspending agent is methocel, hydroxypropyl methylcellulose, di(hydrogenated tallow) phthalic acid amide, a crosslinked maleic anhydride-methyl vinyl ether copolymer, a primary amine including a fatty alkyl moiety having at least 16 carbon atoms, a secondary amine including to fatty alkyl moieties each having at least 12 carbon atoms, or a combination thereof.

37. A method of treating hair to simultaneously cleanse the hair and impart conditioning properties to the hair comprising contacting the hair with a composition comprising:
(a) from about 5% to about 30% by weight of an anionic cleansing surfactant selected from the group consisting of an alkyl sulfate, an alkyl ether sulfate, a sulfate ester of an alkylphenoxy polyoxyethylene ethanol, an alpha-olefin sulfonate, a beta-alkyloxy alkane sulfonate, an alkyl arylsulfonate, an alkyl carbonate, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, an isothienate, and combinations thereof;
(b) from about 0.1% to about 8% by weight of a water-insoluble conditioning agent selected from the group consisting of a nonvolatile silicone having a viscosity of at least 5 centistokes, a volatile silicone having a boiling point of about 150° C. to about 250° C., a volatile hydrocarbon including about 10 to about 26 carbon atoms, and combinations thereof;
(c) from about 0.2% to about 15% by weight of a polyhydric compound selected from the group consisting of glycerol, 1,2,6-hexanetriol, pentaerythritol, inositol, mannitol, sorbitol, and combinations thereof;
(d) about 0.05% to about 0.5% by weight of an anionic emulsifying surfactant having the structure:

$$R_1-O-(A)_xCH_2CO_2^-M^+,$$

wherein $R_1$ is an alkyl or an aralkyl group including about 6 to about 22 carbon atoms, A is an alkylene oxide moiety wherein the alkylene group includes one to about four carbon atoms, X is a number in the range of 5 to about 15, and M is selected from the group consisting of hydrogen, an alkali metal, an alkaline earth metal, ammonium, an alkylammonium, a hydroxyalkylammonium and combinations thereof, wherein the alkyl group includes one to about four carbon atoms;
(e) from about 0.1% to about 1% by weight of a suspending agent selected from the group consisting of methocel, hydroxypropyl methylcellulose, di(hydrogenated tallow) phthalic acid amide, a crosslinked maleic anhydridemethyl vinyl ether copolymer, a primary amine including a fatty alkyl moiety having at least 16 carbon atoms, a secondary amine including two fatty alkyl moieties having at least twelve carbon atoms, and combinations thereof; and
(f) a suitable carrier comprising water.

38. The method of claim 34 wherein $R_1$ is an alkyl or an aralkyl group including from about 5 to about 20 carbon atoms, A is an alkylene oxide moiety wherein the alkylene group includes one to about four carbon atoms, and x is a number in the range of 5 to about 50 15.

* * * * *

UNITED STATES PATENT AND TRADEMARK OFFICE
CERTIFICATE OF CORRECTION

PATENT NO. : 5,275,761

DATED : January 4, 1994

INVENTOR(S) : Bergmann

It is certified that error appears in the above-identified patent and that said Letters Patent is hereby corrected as shown below:

Col. 12, line 1, "1,2,6.hex-" should be --1,2,6-hex- --.

Col. 13, line 38, "about 15, add M" should be --about 15, and M--.

Col. 13, line 67, "and combination thereof" should be --and combinations thereof".

Col. 14, line 3, add a comma after "N.J.".

Col. 14, line 64, "about S to 1" should be --about 5 to 1--.

Col. 16, line 20, "polydiemthylsiloxanes" should be --polydimethylsiloxanes--.

Col. 16, line 30, "SF.1173" should be --SF-1173--.

Col. 20, line 23, "EEA" should be --DEA--.

Col. 20, line 35, "appeal cf" should be --appeal of--.

Col. 20, line 49, "storage an" should be --storage and--.

Col. 23, line 10, "3) Added as a 40 aqueous" should be --3) Added as a 40% aqueous--.

Col. 24, line 38, "a silicone comprising" should be --a silicone conditioning--.

Col. 25, line 32, "1,2,6-hexantriol;" should be --1,2,6-hexanetriol,--.

Col. 27, line 22, "cones having" should be --cone having--.

Col. 28, line 12, "cleans the hair" should be --cleanse the hair--.

UNITED STATES PATENT AND TRADEMARK OFFICE
CERTIFICATE OF CORRECTION

PATENT NO. : 5,275,761

DATED : January 4, 1994

INVENTOR(S) : Bergmann

It is certified that error appears in the above-identified patent and that said Letters Patent is hereby corrected as shown below:

Col. 28, line 27, "thereof:" should be --thereof;--.

Col. 28, line 36, "about 15%" should be --about 15.5%--.

Col. 29, line 1, "claim 27" should be --claim 25--.

Col. 30, line 8, "including to" should be --including two--.

Col. 30, line 46, "X is" should be --x is--.

Col. 30, line 49, "an alkylulam-" should be --an alkylam- --.

Col. 30, line 64, "claim 34" should be --claim 37--.

Col. 30, line 68, "about 50 15." should be --about 15.--.

Signed and Sealed this

Nineteenth Day of July, 1994

*Attest:*

BRUCE LEHMAN

*Attesting Officer*    *Commissioner of Patents and Trademarks*